US00PP25136P2

(12) United States Plant Patent
Wood

(10) Patent No.: US PP25,136 P2
(45) Date of Patent: Dec. 2, 2014

(54) ***HYDRANGEA* PLANT NAMED 'SMHPLQF'**

(50) Latin Name: *Hydrangea paniculata*
Varietal Denomination: SMHPLQF

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 13/987,720

(22) Filed: Aug. 23, 2013

(51) Int. Cl.
*A01H 5/00* (2006.01)

(52) U.S. Cl.
USPC ..... Plt./250

(58) Field of Classification Search
CPC ..... A01H 5/00
USPC ..... Plt./250
See application file for complete search history.

(56) References Cited

PUBLICATIONS

UPOV hit on CA PBR 12-7706 for *hydrangea* plant named 'SMHPLQF' published on Oct. 31, 2012.*

* cited by examiner

*Primary Examiner* — Anne Grunberg
(74) *Attorney, Agent, or Firm* — C. A. Whealy

(57) ABSTRACT

A new and distinct cultivar of *Hydrangea* plant named 'SMHPLQF', characterized by its relatively compact, upright and somewhat outwardly spreading plant habit; strong and sturdy stems; early flowering habit; and inflorescences with light pink-colored sterile flowers that become red purple with development in the autumn.

3 Drawing Sheets

Botanical designation: *Hydrangea paniculata.*
Cultivar denomination: 'SMHPLQF'.

BACKGROUND OF THE INVENTION

The present invention relates to a new and distinct *Hydrangea* plant, botanically known as *Hydrangea paniculata* and hereinafter referred to by the name 'SMHPLQF'.

The new *Hydrangea* plant is a product of a planned breeding program conducted by the Inventor in Grand Haven, Mich. The objective of the breeding program was to develop new *Hydrangea* plants with strong stems and large and attractive inflorescences.

The new *Hydrangea* plant originated from an open-pollination during the spring of 2004 of *Hydrangea paniculata* 'Bulk', disclosed in U.S. Plant Pat. No. 16,812, as the female, or seed parent and an unknown selection of *Hydrangea paniculata* as the male, or pollen, parent. The new *Hydrangea* plant was discovered and selected by the Inventor as a single flowering plant from within the progeny of the stated open-pollination in a controlled environment in Grand Haven, Mich. during the spring of 2009.

Asexual reproduction of the new *Hydrangea* plant by softwood cuttings in a controlled environment in Grand Haven, Mich. since the spring of 2009 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'SMHPLQF'. These characteristics in combination distinguish 'SMHPLQF' as a new and distinct *Hydrangea* plant:

1. Relatively compact, upright and somewhat outwardly spreading plant habit.
2. Strong and sturdy stems.
3. Early flowering habit.
4. Inflorescences with light pink-colored sterile flowers that become red purple with development in the autumn.

Plants of the new *Hydrangea* differ from plants of the female parent, 'Bulk', in the following characteristics:

1. Plants of the new *Hydrangea* are more compact than plants of 'Bulk'.
2. Plants of the new *Hydrangea* flower earlier than plants of 'Bulk'.
3. In the autumn, plants of the new *Hydrangea* have sterile flowers that are red purple in color whereas plants of 'Bulk' have sterile flowers that are dark pink in color.

Plants of the new *Hydrangea* can be compared to plants of *Hydrangea paniculata* 'Pinky Winky', not patented. In side-by-side comparisons, plants of the new *Hydrangea* differed primarily from plants of 'Pinky Winky' in the following characteristics:

1. Plants of the new *Hydrangea* were more compact than plants of 'Pinky Winky'.
2. Plants of the new *Hydrangea* flowered earlier than plants of 'Pinky Winky'.
3. Plants of the new *Hydrangea* had smaller inflorescences than plants of 'Pinky Winky'.

4. In the autumn, plants of the new *Hydrangea* had sterile flowers that were red purple in color whereas plants of 'Pinky Winky' had sterile flowers that were dark pink in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'SMHPLQF' in the summer.

The photograph on the second sheet comprises a side perspective view of a typical flowering plant of 'SMHPLQF' in the autumn.

The photograph on the third sheet is a close-up view of a typical flowering plant of 'SMHPLQF' in the autumn.

DETAILED BOTANICAL DESCRIPTION

Plants used for the aforementioned photographs and the following description were grown during the spring and summer in two-gallon containers in an outdoor nursery in Grand Haven, Mich. and under cultural practices typical of commercial *Hydrangea* production. Plants of the new *Hydrangea* were two years old when the photographs and description were taken. In the following description, color references are made to The Royal Horticultural Society Colour Chart, 2001 Edition, except where general terms of ordinary dictionary significance are used.

Botanical description: *Hydrangea paniculata* 'SMHPLQF'.

Parentage:

*Female, or seed, parent.*—*Hydrangea paniculata* 'Bulk', disclosed in U.S. Plant Pat. No. 16,812.

*Male, or pollen, parent.*—Unknown selection of *Hydrangea paniculata*, not patented.

Propagation:

*Type cutting.*—By softwood cuttings.

*Time to initiate roots, summer.*—About 18 days at temperatures of about 24° C.

*Time to produce a rooted young plant, summer.*—About three months at temperatures of about 24° C.

*Root description.*—Fine and thick; white and brown in color.

*Rooting habit.*—Freely branching; dense.

Plant description:

*Plant form and growth habit.*—Perennial deciduous shrub; relatively compact, upright and somewhat outwardly spreading plant habit; broad inverted triangle; strong and sturdy lateral branches; freely branching habit with about 19 lateral branches per plant; vigorous growth habit.

*Plant height.*—About 68 cm.

*Plant diameter or area of spread.*—About 85 cm.

*Lateral branches.*—Length: About 43 cm. Diameter: About 5 mm. Internode length: About 4 cm. Texture: Smooth, glabrous. Strength: Strong, sturdy. Color: Close to 177A.

Leaf description:

*Arrangement.*—Opposite, simple.

*Length.*—About 8 cm.

*Width.*—About 4.5 cm.

*Shape.*—Ovate.

*Apex.*—Acuminate.

*Base.*—Obtuse.

*Margin.*—Serrulate.

*Texture, upper surface.*—Coarse; pubescent.

*Texture, lower surface.*—Coarse; glabrous.

*Venation pattern.*—Pinnate.

*Color.*—Developing leaves, upper surface: Close to 137C. Developing leaves, lower surface: Close to 138B. Fully expanded leaves, upper surface: Close to 137B; venation, close to 145B. Fully expanded leaves, lower surface: Close to 138B; venation, close to 145C.

*Petioles.*—Length: About 2 cm. Diameter: About 3 mm. Texture, upper and lower surfaces: Smooth, glabrous. Color, upper surface: Close to 59B. Color, lower surface: Close to 145A.

Flower description:

*Flower type and habit.*—Single sterile and fertile flowers arranged on large terminal mophead-type panicles; flowers face upright or outwardly.

*Fragrance.*—Fragrant, pleasant.

*Natural flowering season.*—Continuous flowering throughout the summer in Grand Haven, Mich.

*Quantity of flowers.*—Freely flowering habit; about 250 fertile flowers and about 75 sterile flowers per inflorescence.

*Inflorescence height.*—About 14.5 cm.

*Inflorescence diameter.*—About 13 cm.

*Flower diameter, fertile flowers.*—About 6 mm.

*Flower depth (height), fertile flowers.*—About 5 mm.

*Flower diameter, sterile flowers.*—About 2.3 cm.

*Flower depth (height), sterile flowers.*—About 2 mm.

*Flower buds, fertile and sterile flowers.*—Length: About 5 mm. Diameter: About 3 mm. Shape: Obovate. Color: Close to 155D.

*Petals, fertile flowers only.*—Arrangement: Five in a single whorl. Length: About 4 mm. Width: About 2 mm. Shape: Elliptic. Apex: Acute. Base: Cuneate. Margin: Entire. Texture, upper and lower surfaces: Smooth, glabrous. Color: When opening, upper and lower surfaces: Close to 155D. Fully opened, upper and lower surfaces: Close to 155D.

*Sepals, fertile flowers.*—Quantity per flower: Five in a single whorl. Length: About 3 mm. Width: About 2 mm. Shape: Elliptic. Apex: Acute. Base: Cuneate. Margin: Entire. Texture, upper and lower surfaces: Smooth, glabrous. Color: When opening, upper and lower surfaces: Close to 155A. Fully opened, upper and lower surfaces: Close to 155A.

*Sepals, sterile flowers.*—Quantity per flower: Four in a single whorl. Length: About 1.4 cm. Width: About 1.2 cm. Shape: Obovate. Apex: Retuse. Base: Cuneate. Margin: Entire. Texture, upper and lower surfaces: Smooth, glabrous. Color: When opening, upper and lower surfaces: Close to 51A. Fully opened, upper and lower surfaces: Close to 51A; in the autumn, color becoming progressively closer to 57A.

*Pedicels, fertile flowers.*—Angle: About 50° to 60° from inflorescence axis. Strength: Strong, sturdy. Length: About 6 mm. Diameter: About 1 mm. Texture: Pubescent. Color: Close to 157D.

*Pedicels, sterile flowers.*—Angle: Erect to about 20° from inflorescence axis. Strength: Strong, sturdy.

Length: About 1.5 cm. Diameter: About 1 mm. Texture: Pubescent. Color: Close to 157D.

*Reproductive organs, present on fertile flowers only.*—Stamens: Quantity per flower: About ten. Anther shape: Round. Anther length: About 1 mm. Anther color: Close to 8D. Pollen amount: Scarce. Pollen color: Close to 4D. Pistils: Pistil quantity per flower: About two. Pistil length: About 4 mm. Stigma shape: Round. Stigma color: Close to 10D. Style length: About 1 mm. Style color: Close to 10D. Ovary color: Close to 144D.

*Seeds*.—Quantity per inflorescence: Numerous. Size: Less than 0.1 mm by less than 0.1 mm. Color: Brown.

Disease & pest resistance: Plants of the new *Hydrangea* have been observed to have resistance to root rot pathogens. Plants of the new *Hydrangea* have not been observed to be resistant to pests and other pathogens common to *Hydrangea* plants.

Temperature tolerance: Plants of the new *Hydrangea* have been shown to be tolerant to temperatures ranging from about −30° C. to about 37° C.

It is claimed:

1. A new and distinct *Hydrangea* plant named 'SMH-PLQF' as illustrated and described.

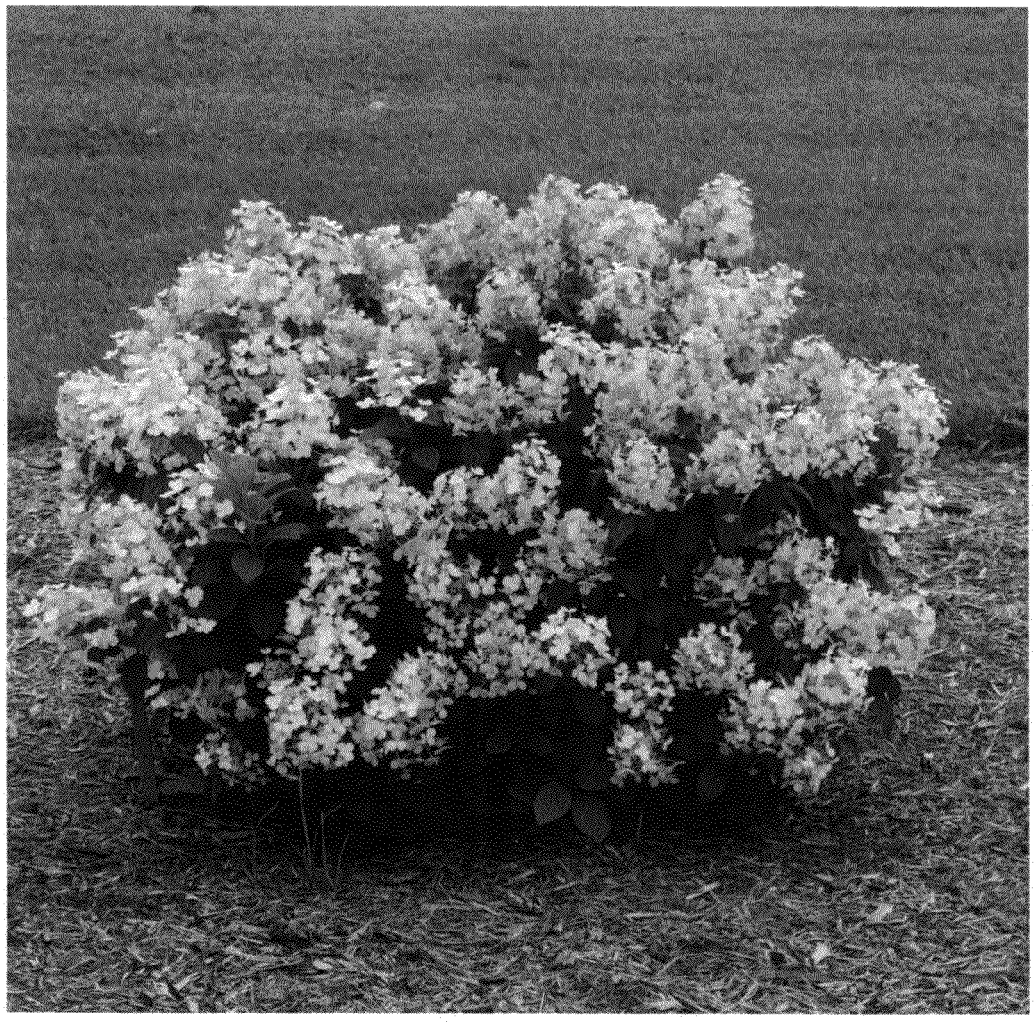

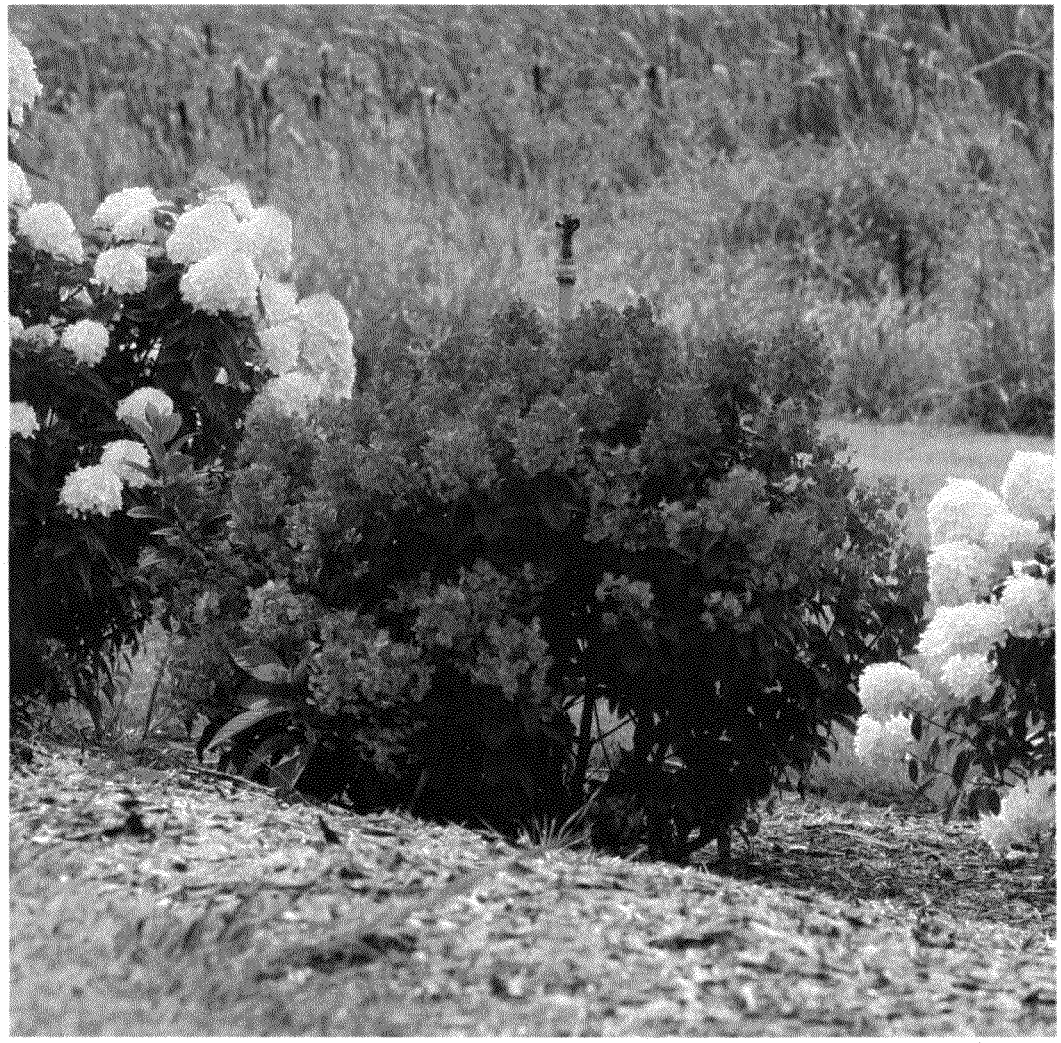

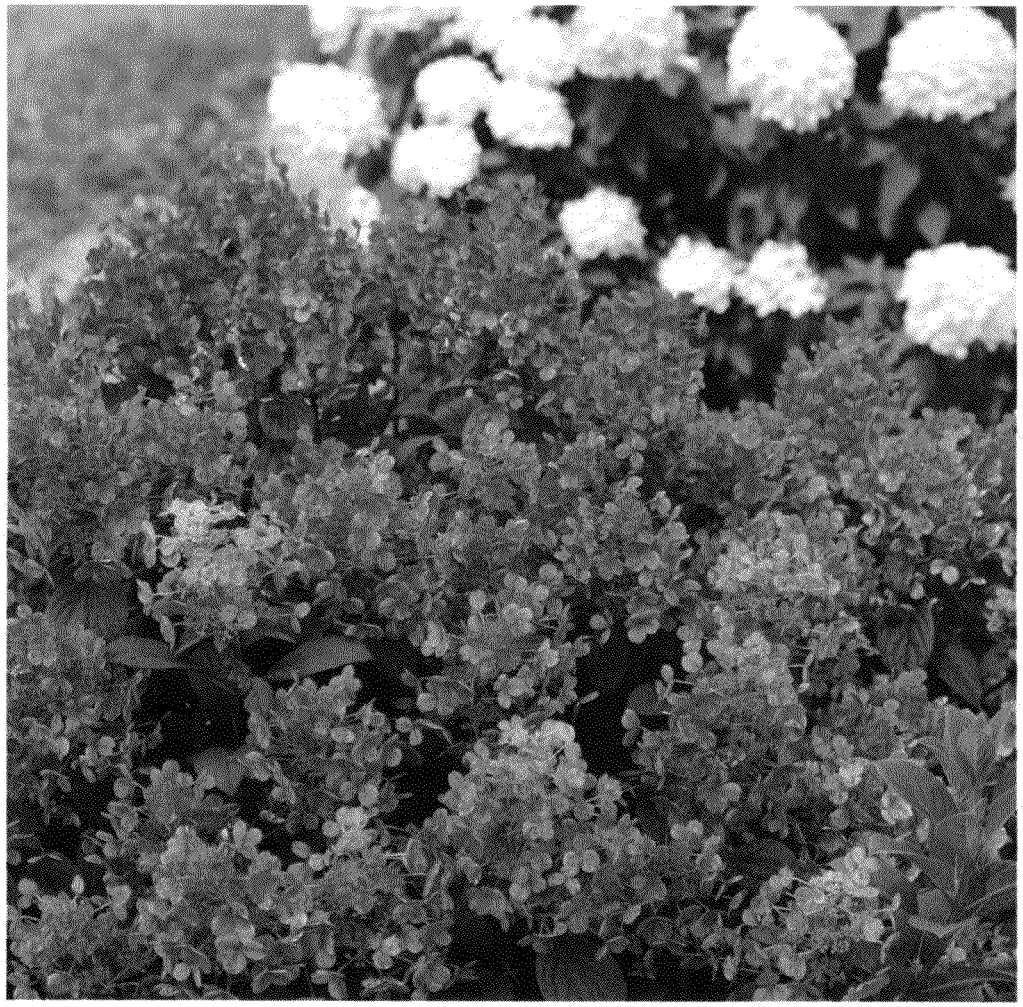

* * * * *